(12) United States Patent
Osypka (10) Patent No.: US 7,467,017 B2
(45) Date of Patent: Dec. 16, 2008

(54) IMPLANTABLE LEAD HAVING ARTICULATED SHOCKING COIL

(75) Inventor: Thomas P. Osypka, Palm Harbor, FL (US)

(73) Assignee: Oscor, Inc., Palm Harbor, FL (US)

( * ) Notice: Subject to any disclaimer, the term of this patent is extended or adjusted under 35 U.S.C. 154(b) by 619 days.

(21) Appl. No.: 11/103,001

(22) Filed: Apr. 11, 2005

(65) Prior Publication Data

US 2005/0228470 A1 Oct. 13, 2005

Related U.S. Application Data

(60) Provisional application No. 60/561,451, filed on Apr. 12, 2004.

(51) Int. Cl.
*A61N 1/05* (2006.01)
(52) U.S. Cl. .................. 607/122; 607/4; 607/5; 607/123; 607/125
(58) Field of Classification Search ............... 607/4, 607/5, 119, 122, 123, 125
See application file for complete search history.

(56) References Cited

U.S. PATENT DOCUMENTS

| | | | | |
|---|---|---|---|---|
| 4,161,952 A | * | 7/1979 | Kinney et al. ............... 607/122 |
| 5,115,818 A | * | 5/1992 | Holleman et al. ........... 607/122 |
| 6,136,021 A | * | 10/2000 | Tockman et al. ............ 607/122 |
| 6,157,862 A | * | 12/2000 | Brownlee et al. ........... 607/123 |
| 2002/0065544 A1 | * | 5/2002 | Smits ......................... 607/122 |
| 2004/0014355 A1 | * | 1/2004 | Osypka et al. .............. 439/502 |
| 2004/0088033 A1 | * | 5/2004 | Smits et al. ................. 607/122 |

* cited by examiner

*Primary Examiner*—Carl H Layno
*Assistant Examiner*—Eugene T Wu
(74) *Attorney, Agent, or Firm*—Scott D. Wofsy; George N. Chaclas; Edwards Angell Palmer & Dodge LLP (57) ABSTRACT

An implantable lead is disclosed which includes an elongated lead body having opposed proximal and distal end portions. At least one defibrillation assembly is operatively associated with the distal end portion of the lead body for delivering electrical energy to cardiac tissue. The defibrillation assembly includes a plurality of axially spaced apart conductive hull assemblies that at least partially surround the elongated lead body, and a helically wound shocking coil that extends over the axially spaced apart hull assemblies so that a series of annular void regions are defined by the shocking coil, the lead body, and adjacent hull assemblies, whereby the annular void regions allow the shocking coil to articulate, thereby inhibiting buckling of the shocking coil.

20 Claims, 6 Drawing Sheets

IMPLANTABLE LEAD HAVING ARTICULATED SHOCKING COIL

CROSS-REFERENCE TO A RELATED APPLICATION

The subject application claims the benefit of priority from U.S. Provisional Patent Application Ser. No. 60/561,451, filed Apr. 12, 2004, the disclosure of which is herein incorporated by reference in its entirety.

BACKGROUND OF THE INVENTION

1. Field of the Invention

The subject invention is directed to cardiac leads, and more particularly, to an implantable defibrillation lead that includes one or more articulated shocking coils for delivering electrical energy to cardiac tissue.

2. Background of the Related Art

An implantable cardioverter defibrillator (ICD) is a device that is implanted in the chest to monitor for and, if necessary, correct episodes of certain types of abnormal heart rhythms (arrhythmia). One example of such an arrhythmia is an exceptionally fast heartbeat (ventricular tachycardia), in response to which an ICD will supply a small amount of electrical energy to stimulate the heart and restore a normal rhythm (i.e., the ICD performs "anti-tachycardia pacing"). This act of converting one heart rhythm to another is called "cardioversion". In more extreme cases, the heartbeat may be so rapid that it amounts to quivering rather than beating; this is called "ventricular fibrillation." To remedy this potentially fatal condition, an ICD performs "defibrillation" by administering a relatively large amount of electrical energy to the heart to restore a normal heartbeat.

In order to perform the above functions, the ICD includes an electrical signal generator and an implantable defibrillation lead for operatively connecting the generator to the heart. The signal generator is contained within a housing that is implanted in the chest of a patient during a surgical procedure. The implantable defibrillation lead is passed through a blood vessel until the distal end of the lead engages the inner surface of the heart. The other (proximal) end connects to the signal generator. In general, these leads include one or more elongated shocking coils located proximate to the distal end and designed to deliver electrical energy from the generator to cardiac tissue upon demand. Typically, such leads further include one or more sensors located proximally to the distal end, which detect the onset of episodes of arrhythmia.

Typically, a shocking coil is formed from one or more conductive wires that are helically wound about a continuous cylindrical section of the lead body. Such coils provide a large surface area for contacting the heart, thereby efficiently delivering energy to the heart when needed. However, one significant disadvantage seen with these prior art coils is that they have a tendency to buckle when the lead body is urged through blood vessels en route to the heart. This buckling stems from the fact that the vessels through which the lead must travel are sinuous, and the varying shape of the vessels provides along their length varying levels of resistance to further forward movement of the lead. As the physician urges the lead through the vessel, the shocking coil may buckle before it can navigate the required turns.

When a shocking coil buckles, it tends to become wider or increase in diameter in a localized area. This decreases the effectiveness of the coil in delivering energy to the heart and can cause localized scaring in adjacent tissue. In addition, such buckling of the coil leads to a local increase in the spacing of adjacent turns of the coil, thereby allowing detrimental tissue ingrowth into the coil. It would be beneficial, therefore, to provide a defibrillation lead having a shocking coil that is not susceptible to buckling during implantation.

SUMMARY OF THE INVENTION

The subject invention is directed to a new and useful implantable lead. The lead includes an elongated body having opposed proximal and distal end portions. At least one articulating defibrillation assembly is operatively associated with the distal end portion of the lead body for delivering electrical energy to cardiac tissue upon demand. A connector assembly is operatively associated with the proximal end portion of the lead body for interacting with an energy-generating device, such as an implantable defibrillator or pulse generator. A conductor assembly extends through the lead body to electrically connect the connector assembly to the defibrillation assembly.

The defibrillation assembly of the subject invention includes a plurality of axially spaced apart conductive hull assemblies and a helically wound shocking coil for delivering energy to tissue. The hull assemblies at least partially surround the elongated lead body. The shocking coil surrounds and is connected to at least one of the plurality of axially spaced apart hull assemblies, such that a series of annular void regions are defined between adjacent hull assemblies, the shocking coil and the lead body. In a preferred embodiment, the shocking coil is connected to each of the plurality of axially spaced apart hull assemblies.

The annular void regions enable the defibrillation assembly to articulate, while inhibiting buckling of the shocking coil as the lead traverses the venous system. In a preferred embodiment, each of the hull assemblies includes two radially inner axially spaced apart support hulls, which at least partially surround the lead body, and a radially outer primary hull, which at least partially surrounds, and is connected to, the support hulls.

The subject invention is also directed to a defibrillation assembly for an implantable lead. The defibrillation assembly includes a helically wound shocking coil for delivering energy to tissue, and a plurality of axially spaced apart stiffening members. The stiffening members are secured to the lead body at locations radially inward of the shocking coil, to allow the defibrillation assembly to articulate as the implantable lead traverses the venous system.

The subject invention is also directed to an implantable lead that includes shocking means for supplying electrical energy to tissue, means for providing alternating regions of stiffness and flexibility to the distal end portion of the lead body in an area occupied by the shocking means, and means for mechanically coupling the shocking means with the means for providing alternating regions of stiffness and flexibility, such that the shocking means is adapted to readily articulate at locations associated with the flexible regions of the distal end portion of the lead body.

These and other aspects of the implantable lead of the subject invention will become more readily apparent to those having ordinary skill in the art from the following detailed description of the invention taken in conjunction with the drawings.

BRIEF DESCRIPTION OF THE DRAWINGS

So that those having ordinary skill in the art to which the present invention pertains will more readily understand how to make and use the implantable lead of the present invention, embodiments thereof will be described in detail hereinbelow with reference to the drawings, wherein.

DETAILED DESCRIPTION OF THE PREFERRED EMBODIMENTS

Figure 1:
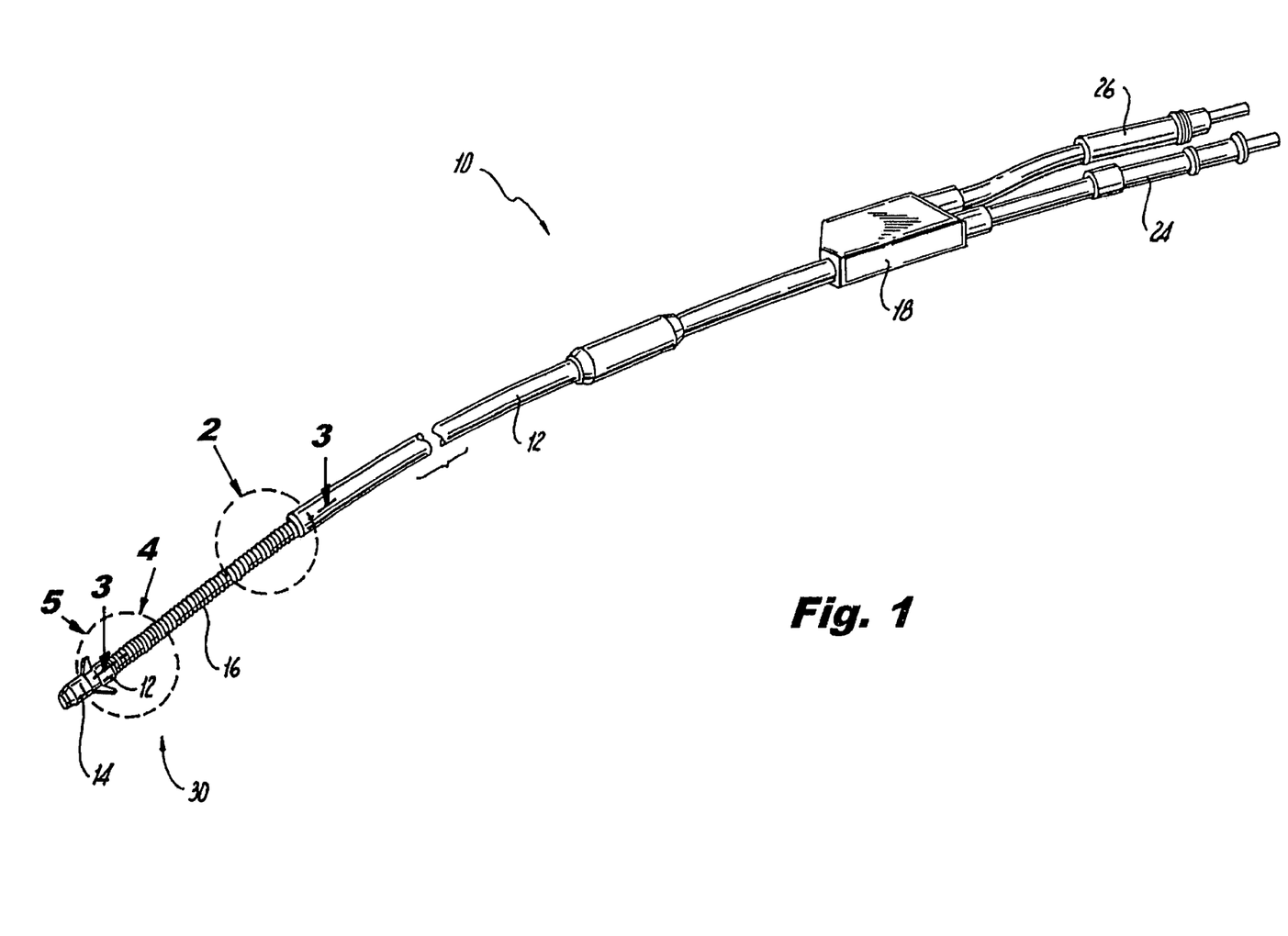
FIG. 1 is a perspective view of an implantable lead designed for defibrillation/cardioversion as well as pacing/sensing, which includes an articulated defibrillation assembly constructed in accordance with a preferred embodiment of the subject invention.

Referring now to the drawings wherein like reference numerals identify similar structural aspects or features of the subject invention, there is illustrated in FIG. 1 an implantable defibrillation lead constructed in accordance with a preferred embodiment of the subject invention and designated generally by reference numeral 10. Lead 10 is typically referred to as a passive fixation lead in that there are a plurality of flexible tines located at the distal end of the lead body to passively secure the lead tip at a desired location within the heart. Alternatively, the lead can be designed for active fixation and include a helical fixation screw at the distal end thereof, which is adapted and configured to engage tissue at a desired location within the heart (see e.g., FIG. 9).

Implantable lead 10 is adapted and configured for pacing/sensing and for defibrillation. Accordingly, lead 10 includes a pacing/sensing electrode 14 located at the distal end of elongated lead body 12, and a shocking coil 16 spaced proximally from the distal pacing/sensing electrode 14. The distal electrode 14 is used for pacing and as a mapping electrode, which senses electrical potentials. One or more additional electrodes may also be associated with the distal end portion of the lead body to facilitate bipolar pacing, including, for example, a ring electrode spaced proximal to the distal electrode 14. Other electrode configurations are also possible and well within the scope of the subject disclosure.

The shocking coil 16 is part of the articulating defibrillation assembly 30 of the subject invention and is designed to deliver electrical energy to cardiac tissue for cardioversion/defibrillation upon demand. It is envisioned that the shocking coil 16 can include one or more adjacently wound conductive elements, so that there is redundancy within the assembly in case an individual element should fail to function properly. Preferably, the lead body 12 is formed from a flexible, biocompatible, insulating material, such as, for example, implantable grade silicone or a similar material.

A connector assembly 18 is operatively associated with the proximal end portion of the elongated lead body 12. Connector assembly 18 is adapted and configured to interact with an energy-generating device, such as, for example, an implantable defibrillator or pulse generator/pacemaker (not shown). Connector assembly is bifurcated and thus it includes two connectors 24 and 26. Connector 24 is associated with the distal pacing electrode 14, while connector 26 is associated with the defibrillation assembly 30. In a preferred embodiment of the subject invention, connector 24 is an IS-1 type connector and connector 26 is a DF-1 type connector 26. Those skilled in the art will readily appreciate that other types of connectors can be employed, such as, for example, LV-1 type connectors and/or DF-4 type connectors, as well as others types known in the art, depending upon the configuration of the lead, for example, if the lead is configured fro unipolar or bipolar pacing and/or defibrillation.

Referring now to FIGS. 2 through 5, lead body 12 includes an exterior sheath 13 and an outer insulating tube 36. Lead body 12 surrounds a conductor assembly 20 that serves to electrically connect the distal pacing/sensing electrode 14 to the IS-1 type connector 24, and the defibrillation assembly 30 to the DF-1 type connector 26. The conductor assembly 20 includes a radially inner conductor coil 44 and a radially outer conductor coil 46. Conductor coils 44, 46 can be formed from one or more filars, e.g., multifilar conductor coils. The radially inner conductor coil 44 connects the distal pacing/sensing electrode 14 to connector 24, and the radially outer conductor coil 44 connects the defibrillation assembly 30 to connector 26.

While the conductor assembly is described as including several conductor coils 44, 46, there is no requirement that the conductors associated with the conductor assembly 20 are coiled. Specifically, in another preferred embodiment, the inner and outer conductors 44, 46 of conductor assembly 20 can be replaced by low resistance multi-standard wires or cables (DFT). In a particular embodiment, such DFT wires extend through multi-lumen tubing in order to connect the defibrillation assembly to an energy-generating device. Alternatively, such DFT wires may each be encased in respective insulation tubes.

Figure 4:
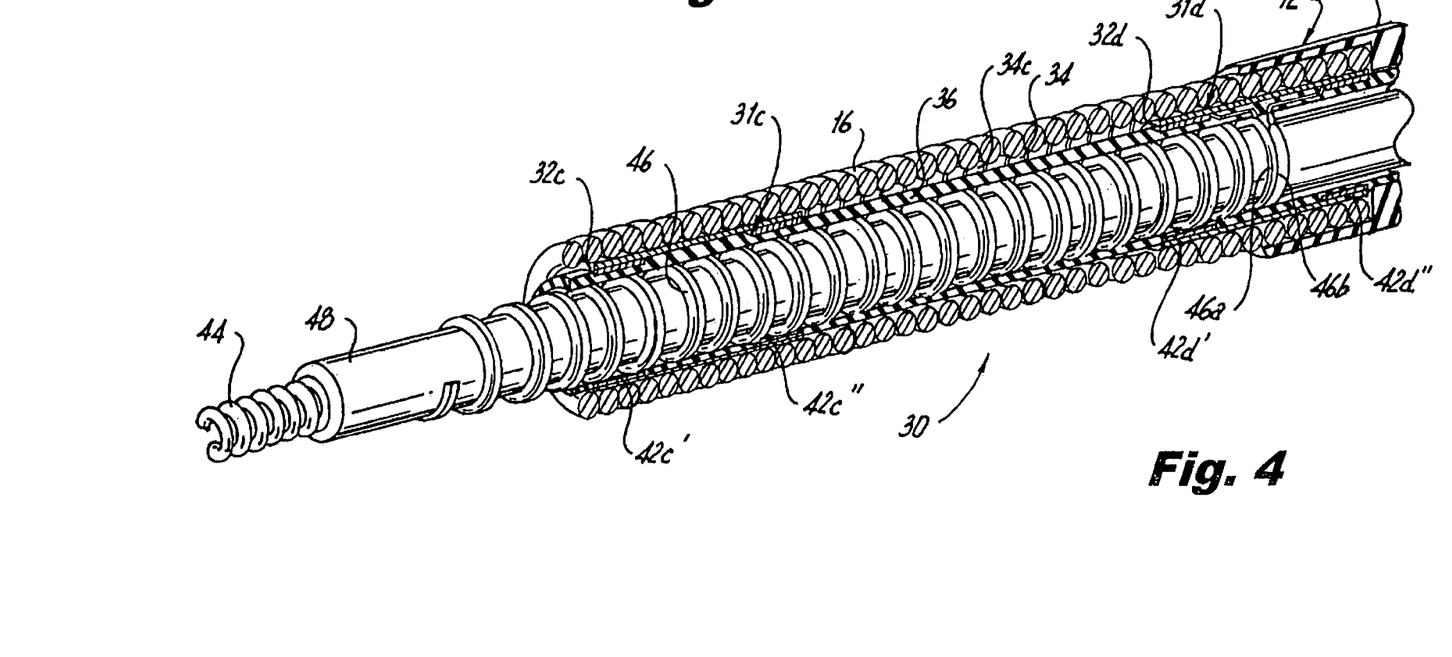
FIG. 4 is a localized perspective view, in cross-section, showing the shocking coil operatively associated with the distal end portion of the implantable lead illustrated in FIG. 1.
Figure 5:
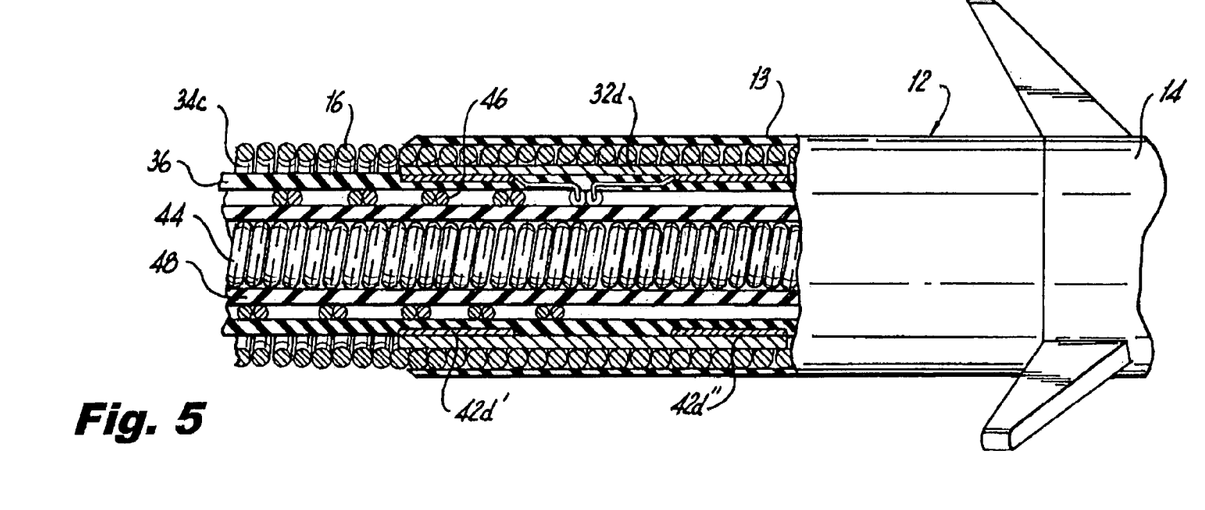
FIG. 5 is a localized cross-sectional view of the distal-most section of the articulated defibrillation assembly shown in FIG. 1, illustrating the connection between the multifilar conductor coil and the distal-most hull assembly.

As best seen in FIG. 4, conductor assembly 20 also includes an inner insulating tube 48, which insulates or otherwise electrically isolates the inner conductor coil 44 of conductor assembly 20 from the outer conductor coil 46 of conductor assembly. The outer insulating tube 36 insulates the radially outer portion of outer conductor coil 46. The inner insulating tube 48 is preferably formed from a flexible, biocompatible, insulating material, such as implantable grade silicone or a similar material.

Figure 3:
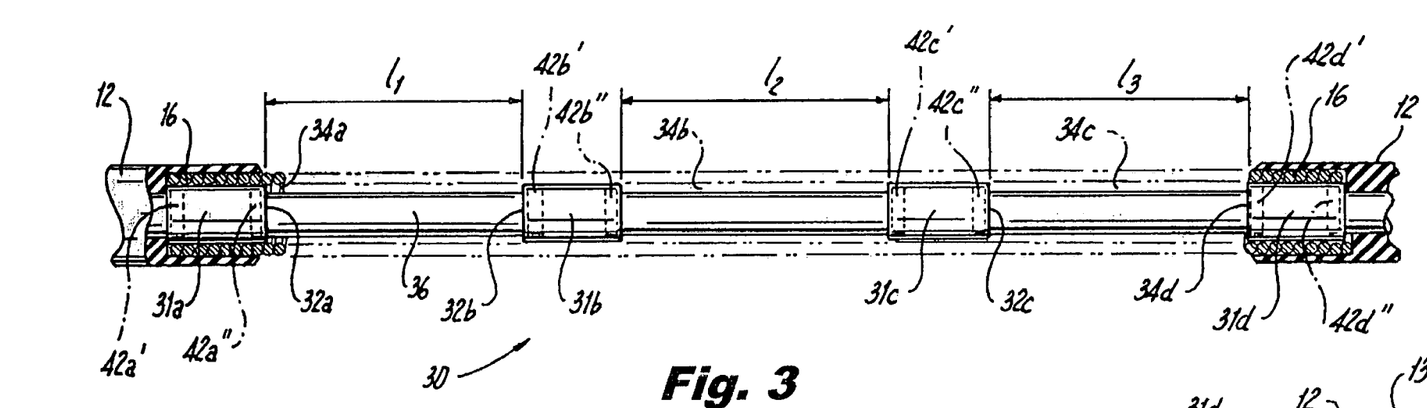
FIG. 3 is a side elevational view in partial cross-section, taken along line 3-3 of FIG. 1, showing the interior features of the articulated defibrillation assembly.

Referring to FIG. 3, the articulated defibrillation assembly 30 of the subject invention includes a plurality of axially spaced apart cylindrical hull assemblies 31a-31d. In this instance, there are four hull assemblies. However, the number of hull assemblies can vary depending upon the axial length of the defibrillation assembly. Alternatively, the size of each or all of the hull assemblies can vary. Each hull assembly is conductive and, as discussed in more detail below, form a conductive bridge between the outer conductor coil 46 and the defibrillation coil 16. As shown, the hull assemblies entirely surround the outer insulating tube 36 of conductor assembly 20. However, it is envisioned that one or more of the hull assemblies can partially or substantially surround the outer insulating tube 36 without departing from the spirit or scope of the subject disclosure.

With continuing reference to FIG. 3, the four hull assemblies 31a-31d, which form part of the articulating defibrillation assembly 30, are axially spaced apart from one another by certain distances, preferably equal distances. For example, the proximal-most hull assembly 31a is separated from hull assembly 31b by a distance $l_1$, medial hull assembly 31b is separated from hull assembly 31c by a distance $l_2$, and medial hull assembly 31c is separated from the distal-most hull assembly 31d by a distance $l_3$. In a particular embodiment, the distances $l_1$, $l_2$, and $l_3$ are all substantially equal. It is envisioned however, that the spacing that exists between adjacent hull assemblies can vary to control the mechanical properties of the defibrillation assembly.

In a preferred embodiment of the subject invention, conductive hull assemblies 31a-31d include respective cylindrical radially outer primary hulls 32a-32d, each of which substantially surrounds and is operatively associated with a pair of corresponding radially inner annular support hulls. For example, as seen in FIG. 4, primary outer hull 32c of medial hull assembly 31c is operatively associated with inner support hulls 42c' and 42c". A similar structural arrangement is disclosed in commonly assigned U.S. Patent Application Publication 2005/0060013, the disclosure of which is incorporated herein by reference in its entirety.

In an embodiment of the subject invention, the radially inner annular support hulls of defibrillation assembly 30 are crimped or otherwise secured to the outer insulating tube 36 of conductor assembly 20 in axially spaced relationship. The support hulls are positioned in coaxial alignment with a corresponding primary hull. The primary hull is joined to the corresponding pair of support hulls by laser welding or by a similar joining technique known in the art.

The helically wound shocking coil 16 of defibrillation assembly 30 extends over or otherwise surrounds the axially spaced part primary hulls 32a-32d and the uncovered sections of the outer insulating tube 36 located therebetween. In one embodiment of the invention, the shocking coil 16 is electrically connected to, or otherwise attached or affixed to, each of the four primary hulls 32a-32d. Other embodiments, however, are also envisioned, in which shocking coil 16 is electrically connected to, or otherwise attached or affixed to, a single one of the primary hulls, or to several of the primary hulls, as desired for either electrical, mechanical, or other performance reasons, such as to provide redundancy in the case of a short.

As noted above, the hull assemblies 31a-31d form a conductive bridge between the radially outer conductor coil 46 of conductor assembly 20 and the shocking coil 16 of defibrillation assembly 30. More particularly, the radially outer conductor coil 46 is connected to one or both of the inner support hulls of one or more of the four hull assemblies, to form a conductive bridge. For example, as shown in FIG. 4, outer conductor coil 46 includes two individual filars 46a, 46b. Filar 46a is electrically connected to annular support hull 42d' while filar 46b is electrically connected to annular support hull 42d" of hull assembly 31d. Such an arrangement provides redundancy should the case arise where one of the two filars of conductor coil 46 becomes short or damaged. Those skilled in the art will readily appreciate that alternative connective arrangements can be employed to form a conductive bridge between the outer conductor coil 46 and the shocking coil 16. An alternative arrangement is shown for example in FIG. 8 and is described in more detail hereinbelow.

Figure 2:
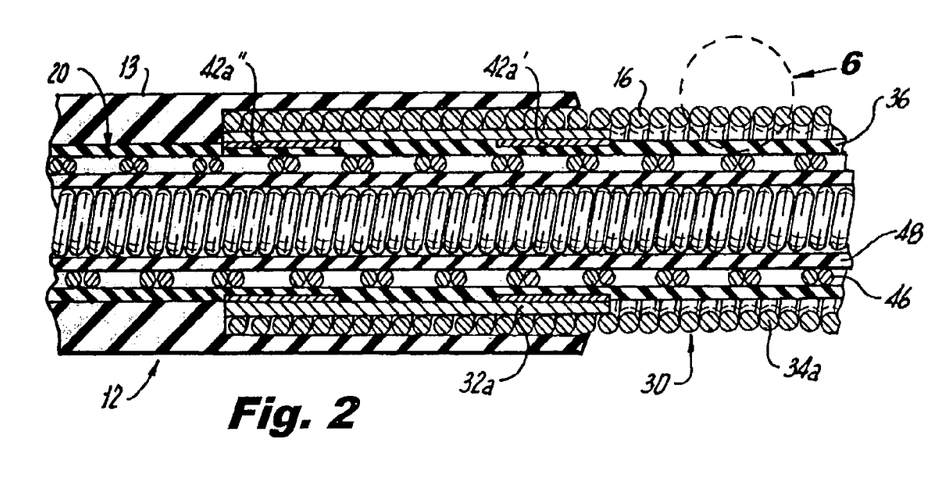
FIG. 2 is a localized cross-sectional view of the proximal-most section of the articulated defibrillation assembly shown in FIG. 1.

As best seen in FIG. 2, the insulating exterior sheath 13 of lead body 12 extends over the proximal-most portion of shocking coil 16 in the region occupied by the proximal-most primary hull 32a. Similarly, as best seen in FIG. 4, insulating exterior sheath 13 extends over the distal-most portion of shocking coil 16 in the region occupied by the distal-most primary hull 32d. These over-laid sections of the exterior sheath 13 provide smooth transition regions between the opposed ends of the shocking coil 16 and the lead body 12, and protect the opposed ends of the shocking coil 16.

As illustrated in FIG. 3, a series of annular void regions 34a-34c of given length are defined or otherwise formed along the length of defibrillation assembly 30. For example, as best seen in FIG. 4, an annular void region 34c is delimited by the interior surface of shocking coil 16, the exterior surface of the insulating tube 36 of lead body 12, and the lateral side surfaces of adjacent hull assemblies 31c, 31d. Similar annular void regions are formed between the other adjacent pairs of hull assemblies, including annular void region 34a formed between the distal-most hull assembly 31a and the medial hull assembly 31b (see FIG. 2), and annular region 34b formed between the two medial hull assemblies 31b and 31c (see FIG. 7).

Figure 6:
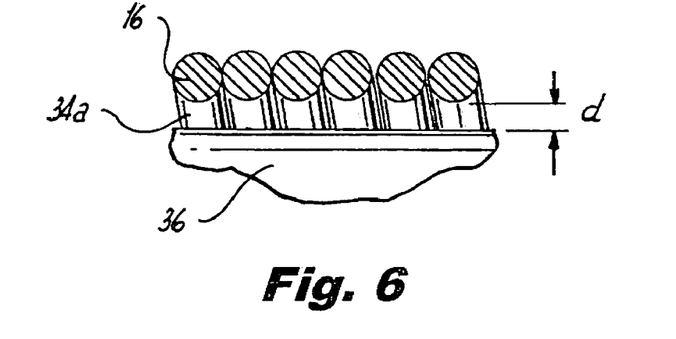
FIG. 6 is a localized cross-sectional view of the shocking coil and outer insulating tube shown in FIG. 5, showing a portion of the annular void between the outer insulating tube and the shocking coil.

As shown in FIG. 6, by way of example, the annular void region 34a of defibrillation assembly 30 has a thickness d defined by the relative diameters of the outer insulating tube 36 and the shocking coil 16. The thickness d of an annular void region 34a can vary depending upon the thickness of the primary hull and/or the thickness of the support hulls associated therewith. In addition, the thickness of a void region can vary depending upon the magnitude of the force used to crimp an inner support hull around the outer insulating tube 36. The widths of the three annular void regions 34a-34c shown in FIG. 3 are denoted by the distances $l_1$, $l_2$ and $l_3$. These distances can vary depending upon the size, number and relative placement of the four hull assemblies 31a-31 d.

In the distal end portion of the lead body 12 occupied by the defibrillation assembly 30, the hull assemblies 31a-31d provide incremental areas of relative stiffness, while the annular void regions 34a-34c located between adjacent pairs of hull assemblies provide incremental regions of relative flexibility. The articulated shocking coil 16 is therefore configured to be urged or otherwise delivered through the somewhat sinuous coronary blood vessels during implantation, without buckling in a manner that increases the outer diameter of the coil in a localized area.

Figure 7:
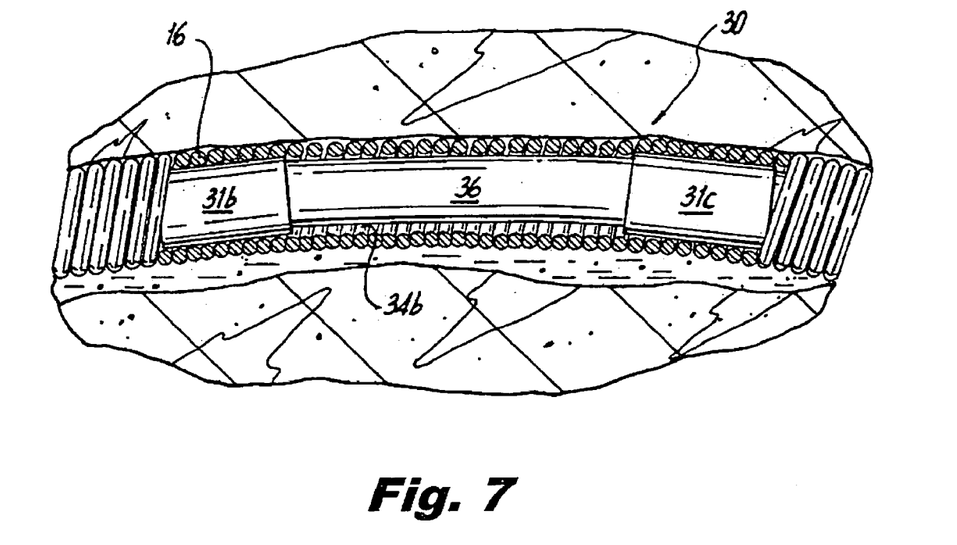
FIG. 7 is a cross-sectional view of the lead of FIG. 1, during implantation, showing the articulation of the defibrillation assembly as it traverses a venous system.

Moreover, as shown in FIG. 7, during implantation, defibrillation assembly 30 articulates or otherwise freely bends at the locations in which the annular void regions are present, for example, in the area of annular void region 34b. That is, rather than buckle or bulge outwardly when traversing a curvature in the blood vessel due to stiffness, the shocking coil 16 conforms to the void region 34b created between adjacent hull assemblies 31b, 31c. At the same time, the hull assemblies provide sufficient stiffness within the defibrillation assembly 30 to enable the lead body 12 to be urged forward without collapsing or buckling. By inhibiting buckling of the coil 16, the problem of increased spacing of the turns of the coil 16 is reduced, as is the related problem of tissue ingrowth into the coil 16.

It is envisioned that the mechanical and/or physical properties of the defibrillation assembly 30 can be optimized or varied by the designer of the device. For example, in instances where increased stiffness is desired, the hull assemblies can be wider or placed closer together or a greater number of hull assemblies can be employed. Alternatively, in instances where the lead is required to be more flexible, the hull assemblies can be placed farther apart from one another or fewer hull assemblies may be employed, so long as the lead body maintains a requisite stiffness in the area occupied by the defibrillation assembly.

Figure 8:
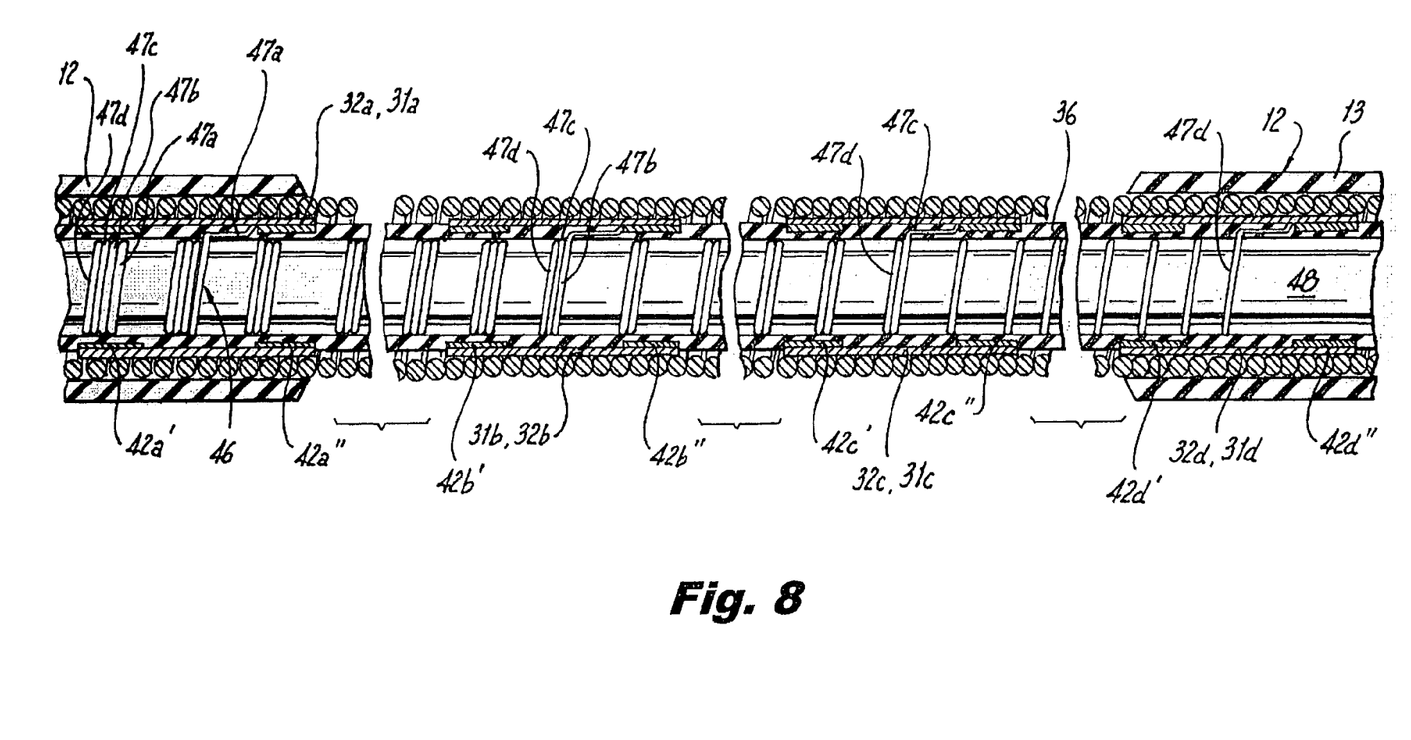
FIG. 8 is a cross-sectional view of the defibrillation assembly of the subject invention, which is powered by a quadrifilar coil, and wherein each hull assembly is powered by one of the four filars.

Referring to FIG. 8, in an embodiment of the subject invention, the outer conductor coil 46 is a quadrafilar conductor coil, hence it includes four conductive filars 47a-47d. In this embodiment, each conductive filar is operatively associated with or otherwise electrically connected to a respective one of the hull assemblies 31a-31d. More particularly, a first filar 47a is electrically connected to the inner support hull 42a" of the proximal-most hull assembly 31a, a second filar 47b is electrically connected to the inner support hull 42b' of medial hull assembly 31b, a third filar 47c is electrically connected to the inner support hull 42c" of medial hull assembly 31c and a fourth filar 47d is electrically connected to the inner support hull 42d" of the distal-most hull assembly 31d. Alternative connective arrangements for quadrifilar coils or other multifilar coils are also envisioned and within the scope of the subject disclosure.

Figure 9:
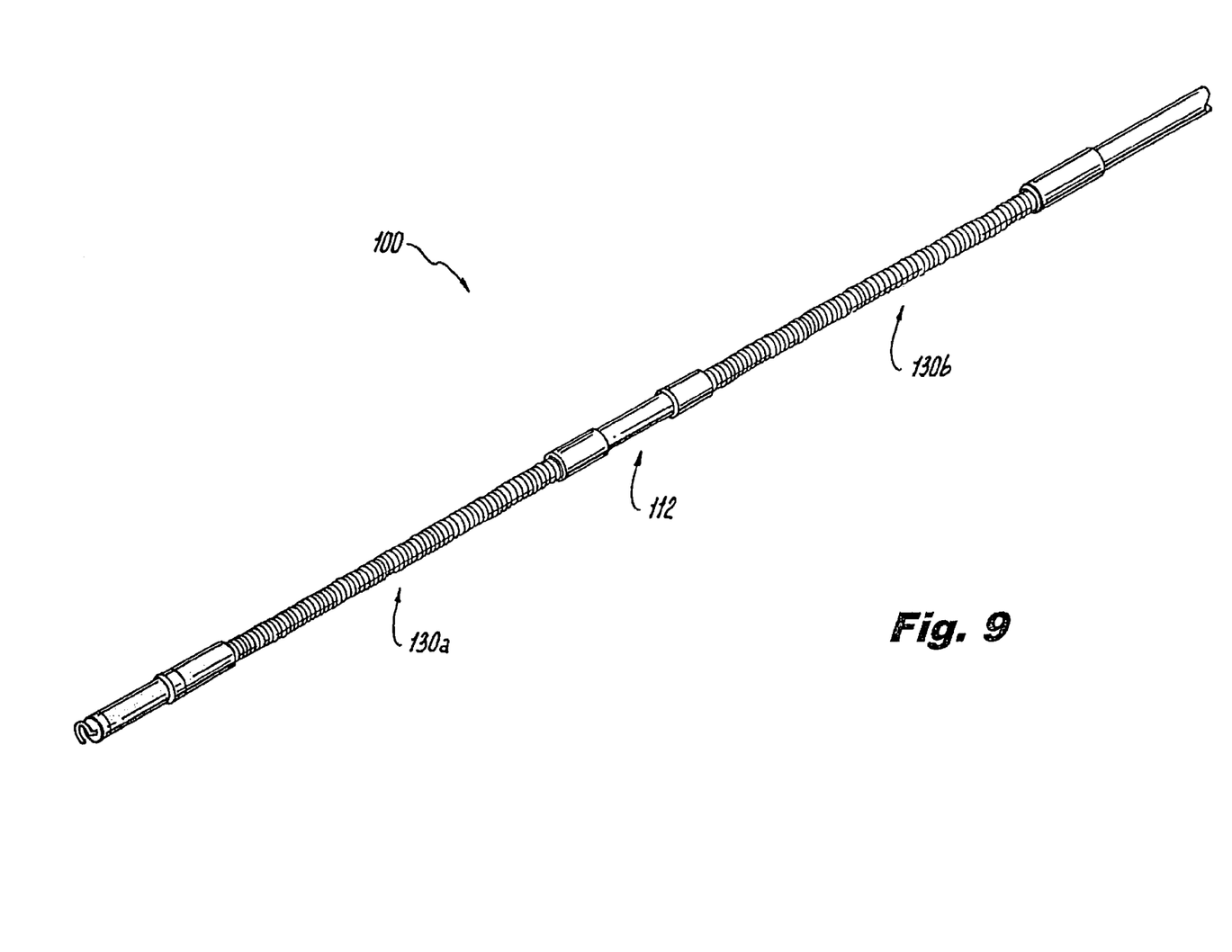
FIG. 9 is a side elevational view of another preferred embodiment of the subject invention, showing a lead having two separate articulating defibrillation assemblies.

Referring now to FIG. 9, there is illustrated a distal end portion of another implantable lead constructed in accordance with a preferred embodiment of the subject invention and designated generally by reference numeral 100. Lead 100 includes a lead body 112 having two axially spaced apart articulating defibrillation assemblies 130a and 130b constructed in accordance with a preferred embodiment of the subject invention. In this instance, it is envisioned that the defibrillation assemblies 130a, 130b can be powered either cooperatively or independently. That is, each articulating defibrillation assembly could have a separate conductor assembly associated therewith or a common conductor assembly could power the two assemblies. In another embodiment of the subject invention, there may be more than two defibrillation assemblies with shocking coils powered either independently or cooperatively.

Other methods or structures for providing incremental areas of stiffness and flexibility are also envisioned and within the scope of the subject disclosure. For example, stiffening members other than or in addition to the cylindrical hull assemblies described herein may be employed at incremental locations underlying the shocking coil of the articulating defibrillation assembly. These features may be arranged coaxially with the shocking coil or they may be included at one or more off-axis locations. Such stiffening members could take the form of small cylinders or rings that me be formed from a conductive material or from a non-conductive material such as a ceramic or plastic.

Although the implantable defibrillation lead of the subject invention has been described with respect to preferred embodiments, those skilled in the art will readily appreciate that changes and modifications may be made thereto without departing from the spirit and scope of the subject invention as defined by the appended claims.

What is claimed is:
1. An implantable lead comprising:
   a) an elongated lead body having opposed proximal and distal end portions;
   b) a connector assembly operatively associated with the proximal end portion of the lead body for interacting with an energy-generating device;
   c) at least one defibrillation assembly operatively associated with the distal end portion of the lead body for delivering electrical energy to cardiac tissue, and including:
      i) a plurality of axially spaced apart conductive hull assemblies at least partially surrounding the elongated lead body; and
      ii) a helically wound shocking coil extending over the axially spaced apart hull assemblies so that a series of annular void regions are defined by the shocking coil, the lead body, and adjacent hull assemblies, the annular void regions allowing the shocking coil to articulate and thereby inhibiting buckling of the shocking coil; and
   d) a conductor assembly extending through the lead body that electrically connects the connector assembly to the defibrillation assembly.

2. An implantable lead as recited in claim 1, wherein the conductor assembly is electrically connected to at least one of the plurality of axially spaced apart conductive hull assemblies.

3. An implantable lead as recited in claim 1, wherein the shocking coil is connected to at least one of the plurality of axially spaced apart conductive hull assemblies.

4. An implantable lead as recited in claim 1, wherein the shocking coil is connected to each of the plurality of axially spaced apart conductive hull assemblies.

5. An implantable lead as recited in claim 1, wherein each hull assembly includes two radially inner axially spaced apart support hulls, which at least partially surround the lead body, and a radially outer primary hull, which at least partially surrounds, and is connected to, the support hulls.

6. An implantable lead as recited in claim 1, wherein the plurality of axially spaced apart hull assemblies includes at least four hull assemblies.

7. An implantable lead as recited in claim 1, wherein the conductor assembly includes a plurality of adjacently wound conductors arranged in a multifilar coil, the multifilar coil connecting at least one of the plurality of axially spaced apart hull assemblies to the connector assembly.

8. An implantable lead as recited in claim 7, wherein each of the plurality of axially spaced apart hull assemblies is electrically connected to a respective one of said plurality of conductors of the multifilar coil.

9. An implantable lead as recited in claim 1, further comprising a pacing/sensing electrode operatively associated with the distal end portion of the lead body and electrically connected to the conductor assembly.

10. An implantable lead as recited in claim 9, wherein the conductor assembly includes a first conductor means, which electrically connects the pacing/sensing electrode to the connector assembly, and a second conductor means, which electrically connects at least one of the plurality of axially spaced apart hull assemblies to the connector assembly.

11. An implantable lead as recited in claim 1, wherein the helically wound shocking coil includes at least two adjacently wound conductive elements.

12. An implantable lead as recited in claim 1, wherein the lead includes first and second axially spaced apart defibrillation assemblies, each of which includes a separate shocking coil and associated hull assemblies operatively associated with the connector assembly and the conductor assembly.

13. A defibrillation assembly for an implantable lead having an elongated lead body and a conductor disposed within the lead body, the defibrillation assembly comprising:
   a) a helically wound shocking coil for delivering energy to tissue, the shocking coil electrically connected to the conductor; and
   b) a plurality of axially spaced apart stiffening members secured to the lead body at locations radially inward of the shocking coil so that a series of annular void regions are defined by the shocking coil, the lead body, and adjacent stiffening members, the stiffening members allowing the defibrillation assembly to articulate as the implantable lead traverses a venous system.

14. An implantable lead having an elongated lead body, comprising:
- a) shocking means operatively associated with a distal end portion of the elongated lead body for supplying electrical energy to tissue;
- b) means for providing alternating regions of stiffness and flexibility to the distal end portion of the lead body in an area occupied by the shocking means; and
- c) means for mechanically coupling the shocking means with the means for providing alternating regions of stiffness and flexibility so that a series of annular void regions are defined by the shocking means, the lead body, and the means for providing stiffness and flexibility, such that the shocking means can readily articulate at locations associated with the flexible regions of the lead body.

15. An implantable lead as recited in claim 14, wherein the shocking means includes at least two independently powered shocking coils.

16. An implantable lead as recited in claim 15, wherein the two independently powered shocking coils are axially spaced apart from one another.

17. A defibrillation assembly for an implantable lead having an elongated lead body, the defibrillation assembly comprising:
- a) a plurality of conductive cylindrical hulls at least partially surrounding the elongated lead body at axially spaced apart locations; and
- b) a helically wound shocking coil surrounding the plurality of axially spaced apart cylindrical hulls such that annular void regions are defined by the shocking coil, the lead body, and adjacent cylindrical hulls, whereby the annular void regions allow the defibrillation assembly to articulate and thereby inhibit buckling of the shocking coil.

18. A defibrillation assembly as recited in claim 17, wherein the helically wound shocking coil is connected to at least one of the plurality of axially spaced apart cylindrical hulls.

19. A defibrillation assembly as recited in claim 17, wherein the helically wound shocking coil is connected to each of the plurality of axially spaced apart cylindrical hulls.

20. A defibrillation assembly as recited in claim 17, wherein the helically wound shocking coil includes at least two adjacently wound conductive elements.

* * * * *